United States Patent [19]

Baydar

[11] Patent Number: 4,857,310
[45] Date of Patent: Aug. 15, 1989

[54] TRIGLYCERIDE QUATERNARY AMMONIUM COMPOUNDS, THEIR PREPARATION AND USE

[75] Inventor: Ahmet E. Baydar, London, England
[73] Assignee: The Gillette Company, Boston, Mass.
[21] Appl. No.: 170,965
[22] Filed: Mar. 21, 1988
[30] Foreign Application Priority Data
  Mar. 25, 1987 [GB] United Kingdom ................. 8707055
[51] Int. Cl.$^4$ ......................... A61K 7/08; A61K 7/48; A61K 31/14; C11C 3/00
[52] U.S. Cl. .................................. 424/70; 260/404.5; 514/547; 514/597; 514/786
[58] Field of Search ................... 260/404.5 Q; 424/70; 514/547, 597, 786

[56] References Cited

U.S. PATENT DOCUMENTS

| | | | |
|---|---|---|---|
| 3,873,583 | 3/1975 | Walz et al. | 260/404 |
| 3,959,461 | 5/1976 | Bailey et al. | 424/70 |
| 4,220,581 | 9/1980 | Cooperman et al. | 260/404.5 Q |
| 4,274,987 | 6/1981 | Augustyn | 524/425 |
| 4,464,400 | 8/1984 | Kimura et al. | 514/786 |
| 4,552,754 | 11/1985 | Muramatsu et al. | 424/70 |
| 4,721,728 | 1/1988 | Bruzzese et al. | 514/547 |
| 4,743,621 | 5/1988 | Cavazza | 514/547 |

OTHER PUBLICATIONS

Roberts and Caserio, *Organic Chemistry*, 1965 (W. A. Benjamin, Inc., New York), pp. 560, 563.

*Primary Examiner*—Werren B. Lone
*Assistant Examiner*—Vera C. Clarke
*Attorney, Agent, or Firm*—Mandel E. Slater

[57] ABSTRACT

Novel triglyceride quaternary ammonium compounds are provided according to formula I,

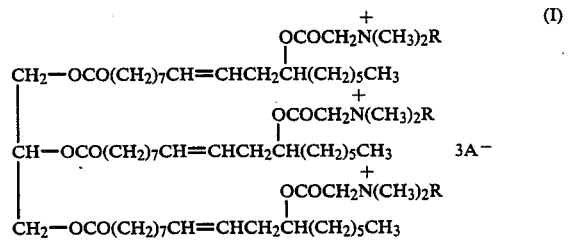

in which R is an alkyl group having 10 to 20 carbon atoms, preferably n-dodecyl or n-octadecyl, and $A^-$ is a physiologically acceptable anion, preferably chloride. These compounds are prepared by a process which essentially comprises reacting triglyceryl ricinoleate with chloroacetyl chloride to esterify the hydroxyl groups of the triglyceride and then reacting the product obtained with an alkyldimethylamine of the formula $N(CH_3)_2R$. The compounds of formula I are useful as additives to skin moisturizing compositions and hair conditioners.

10 Claims, No Drawings

TRIGLYCERIDE QUATERNARY AMMONIUM COMPOUNDS, THEIR PREPARATION AND USE

BACKGROUND OF THE INVENTION

1. Field of the Invention

This invention is concerned with certain novel triglyceride quaternary ammonium compounds, with a process for their preparation, and with their use in cosmetic and toiletry compositions.

2. Description of the Prior Art

Many cosmetic and toiletry compositions contain natural triglyceride oils, that is the glyceryl esters of naturally occurring long chain fatty acids, but in certain types of composition, such as moisturizing compositions, it is found that certain triglyceride oils are not readily absorbed by the skin. Such slow or reduced absorption of triglyceride oils may reduce the acceptability of cosmetic or toiletry compositions containing them even though the other properties and characteristics of the compositions are favorable.

SUMMARY OF THE INVENTION

It would, therefore, be desirable to have available an additive which causes natural triglyceride oils to be more readily absorbed by the skin and which is completely compatible with such triglycerides. An object of the invention is to provide a range of such additives.

We have now found that triglyceride quaternary ammonium compounds of formula I,

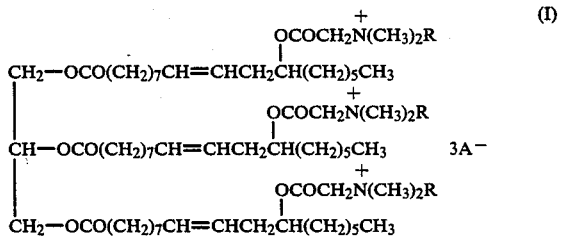

in which R is an alkyl group having 10 to 20 carbon atoms, and $A^-$ is a physiologically acceptable anion, have a range of useful properties. Thus the compounds in which R is an alkyl group having 16 to 20 carbon atoms, when added to natural triglyceride oils, render the latter more readily absorbed by the skin and are completely compatible with such oils; those compounds also have useful hair conditioning properties. The compounds of formula I in which R is an alkyl group containing 10 to 12 carbon atoms have valuable bactericidal properties.

The triglyceride quaternary ammonium compounds of formula I are novel compounds and constitute one aspect of the present invention.

The anion $A^-$ is preferably chloride, but may be any other physiologically acceptable anion which does not interfere with and is compatible with the composition in which the compound is used.

Particularly preferred compounds of formula I are those in which R is a linear alkyl group containing 12 or 18 carbon atoms, that is n-dodecyl or n-octadecyl (stearyl).

The compounds of formula I are not soluble in water, but are readily self-emulsified in water. They are very soluble in ethanol and soluble in iso-propanol, propanol, acetone and chloroform, and in hot ethyl acetate. They range from viscous oils to low melting, waxy solids.

According to another aspect of the invention, there is provided a process for the preparation of a triglyceride quaternary ammonium compound of formula I, which comprises reacting triglyceryl ricinoleate with chloracetyl chloride to esterify the hydroxyl groups of the triglyceride, and reacting the product obtained with an alkyldimethylamine of the formula $N(CH_3)_2R$, where R has the above-stated meaning.

This process gives compounds of formula I in which $A^-$ is chloride. These chlorides may be converted into salts having other anions, such as sulfate, by conventional procedures.

Triglyceryl ricinoleate is the major component of castor oil, the fatty acid content of which is typically as follows, by weight:

| | |
|---|---|
| ricinoleic | 87% |
| oleic | 7% |
| linoleic | 3% |
| palmitic | 2% |
| stearic | 1% |

The process according to the invention is preferably carried out with castor oil, rather than with pure triglyceryl ricinoleate; the other trigylcerides present in castor oil are unaffected by the reactions and are present with the desired quaternary ammonium compound in the product. Such an impure product is entirely suitable for use in the various applications, such as cosmetic and toiletry compositions, described herein.

The first stage of the process according to the invention may be carried out at room temperature or moderately elevated temperatures. Both the starting materials, that is, triglyceryl ricinoleate (or castor oil) and chloroacetyl chloride are liquid, and the reaction mixture may consist simply of the two reactants. One or more organic solvents for the reactants may be present, if desired, suitable solvents being, for example, toluene, chloroform, or dichloromethane. It is generally preferred to use a stoichimetric excess of the chloroacetyl chloride, that is, an excess over and above the 3 moles of chloroacetyl chloride required to react with 1 mole of triglyceryl ricinoleate; it is preferred to use an excess of 2 to 5 moles. Unreacted chloroacetyl chloride may be removed from the first stage product by repeated washings with an aqueous solution of an alkali, such as sodium bicarbonate.

The second stage of the process is generally carried out in the presence of a suitable organic solvent, such as ethanol, at an elevated temperature. It is preferred to use the stoichiometric quantity of the amine.

The triglyceride quaternary ammonium compounds of formula I in which R is $C_{16}$–$C_{20}$ alkyl are valuable additives to a range of cosmetic and toiletry compositions. They are particularly useful in moisturizing compositions containing natural triglycerides which are not easily absorbed by the skin. Examples of such natural triglycerides are avocado oil and apricot kernel oil which are the major natural triglyceride oil components of certain commercially available moisturizing lotions and creams. By replacing 20% by weight of the avocado oil or apricot kernel oil in such compositions by the formula I compound in which R is stearyl, a significant improvement in the absorption of the composition by the skin is obtained.

The compounds of formula I in which R is $C_{16}$–$C_{20}$ alkyl can also be used in hair conditioning compositions as the active hair conditioning component thereof. Their activity for this purpose is shown by conventional wet combing and fly-away tests and measurement of combing work.

The compounds of formula I in which R is $C_{12}$ alkyl also have useful anti-microbial activity, particularly against Gram positive bacteria. The compound, propane-1,2,3-tri[octadec-9-en-12-(oxycarbonyl-N-methylene-N,N-dimethyl-N-dodecylammonium chloride)oate], formula I, R=n-dodecyl, A$^-$=chloride (see Example 2 below), was subjected to the standard minimum inhibitory concentration (MIC) tests against a range of common microorganisms. The results obtained are as follows (MIC values in ppm/ug):

|  | MIC |
| --- | --- |
| Staphylococcus aureus | 60 |
| Candida albicans | 250 |
| Aspergillus wentii | 500 |
| Pseudomonas putida | 2000 |
| Proteus rettgeri | 2000 |

The first two of these organisms are Gram positive bacteria, the third is a fungus, and the fourth and fifth are Gram negative bacteria.

In order that the invention may be more fully understood, the following examples are given by way of illustration only.

EXAMPLE 1

(i) Preparation of propane-1,2,3-tri[octadec-9-en-12-(oxycarbonyl-chloromethane)oate]

Castor oil (20 g) was stirred at room temperature for 12 hours with chloroacetyl chloride (45 ml). The reaction mixture was taken up in ether, the ethereal solution was washed with aqueous sodium bicarbonate (x8), water (x2), and then dried. The solvent was removed under reduced pressure to yield propane-1,2,3-tri[octadec-9-en-12-(oxycarbonylchloromethane)oate] as a viscous orange oil (21.2 g).

3 g of the oil was purified by column chromatography using silica gel and ethyl acetate (10%) and 60–80 petroleum ether (90%) as eluant. The pure chloro derivative was dried in a vacuum oven at 100° C. for 24 hours.

IR: 1740 (C=O), 1725 (C=O) cm$^{-1}$

NMR: δ5.41–5.56 (m, 3H, CH=), 5.23–5.39 (m, 3H, CH=) 5.26–5.33 (m, 1H, CH—O), 4.90–4.97 (pentet, 3H, CH—OCO), 4.31 (pseudo d, 2H, $CH_2$—O), 4.19 (pseudo d, 2H, $CH_2$—O), 4.03 (s, 6H, $OCH_2Cl$), 2.26–2.39 (m, 12H, $6XCH_2$—C=C), 2.03–2.09 (m, 6H, $3XCH_2C$=O), 1.2–1.6 (m, 6OH, 30×$CH_2$), 0.94 (t, 9H, Me) ppm. (s=singlet, d=doublet, t=triplet, m=multiplet, br=broad)

| Analysis: | Required | Found |
| --- | --- | --- |
| % C | 65.05 | 65.16 |
| % H | 9.29 | 9.38 |
| % Cl | 9.15 | 8.68 |

(ii) Preparation of propane-1,2,3-tri[octadec-9-en-12-(oxycarbonyl-N-methylene-N,N-dimethyl-N-octadecylammonium chloride)oate]

The crude chloro derivative from (i) (11.6 g, 0.01M) and stearyl dimethylamine (8.94 g, 0.03M) were refluxed in 100 ml of ethanol for 90 hours. The solvent was removed under reduced pressure and the residue was dried under vacuum at 80° C. to give a viscous oil which solidified into a wax on standing (yield: 18.9 g). This product was 88% quaternary ammonium salt, that is, propane-1,2,3-tri[octadec-9-en-12-(oxycarbonyl-N-methylene-N,N-dimethyl-n-octadecylammonium chloride)oate], the remainder being the triglycerides of fatty acids other than ricinoleic acid present in castor oil.

The pure chloro derivative as obtained by chromatography, see (i), (1.16 g, 0.001M) and stearyldimethylamine (0.894 g, 0.003M) were refluxed in 20 ml of ethanol for 90 hours. The product was worked up as for the crude derivative.

Yield: 2.01 g (98%)

IR: 1740(C=O), 1640(C=C)cm$^{-1}$

NMR: δ5.4–5.6 (m, 3H, CH=), 5.34–5.38 (m, 3H, CH=), 5.12 (m, 1H, CHO), 4.97 (m, 3H, CHO—OCO), 4.2–4.4 (pseudo d, 4H, $CH_2$—O), 3.5 (s, 6H, O—$CH_2$—N$^+$), 2.15–2.4 (m, 12H, 6X $CH_2$—C=C), 2.0 (m, 6H, 3X $CH_2$C=O), 1.1–1–9 (brs, 189H), 0.95(t, 9H, 3xMe).

| Analysis: | Required: | Found: |
| --- | --- | --- |
| % C | 71.85 | 71.89 |
| % H | 11.6 | 11.83 |
| % N | 2.05 | 1.96 |

EXAMPLE 2

Preparation of propane-1,2,3-tri[octadec-9-en-12-(oxycarbonyl-N-methylene-N,N-dimethyl-N-dodecylammonium chloride)oate]

The pure chloro derivative from Example 1(i) (11.6 g, 0.01M) and N,N-dimethyldodecylamine (6.39 g, 0.03M) were refluxed in 100 ml of ethanol for 72 hours. The solvent was removed under reduced pressure and the residue was dried under vacuum at 80° C. to give propane-1,2,3-tri[octadec-9-en-12-(oxycarbonyl-N-methylene-N,N-dimethyl-n-dodecylammonium chloride)oate] as a viscous oil.

Yield: 17.1 g (95%)

IR: 330–2500 (br), 1730 (C=O), 1200 cm$^{-1}$

NMR: δ5.43–5.55 (m, 3H, CH=), 5.38–5.40 (m, 3H, CH=), 5.18–5.23 (m, 1H, CH—O), 4.96 (p, 3H, CH—OCO, 4.2–4.35 (pseudo d, 4H, $CH_2$—O), 3.53 (s, 6H, O—$CH_2N^+$), 2.15–2.32 (m, 12H, 6X $CH_2$—C=C), 1.95–2.01 (m, 6H, 3X $CH_2$—C=O), 1.2–1.6 (m, 153H), 0.92 (t, 9H, Me).

| Analysis: | Required | Found |
| --- | --- | --- |
| % C | 69.94 | 69.97 |
| % H | 11.11 | 11.37 |
| % N | 2.3 | 2.36 |

EXAMPLE 3

Moisturizing Lotion

A moisturizing lotion consisting of an oil-in-water emulsion of the following composition (all percentages on a weight/weight basis) was made up.

| | % |
|---|---|
| Aqueous phase | |
| Deionized water | 85.2 |
| Propylene glycol | 2.0 |
| Carbopol 941 | 0.2 |
| Triethanolamine | 0.6 |
| Methyl paraben | 0.15 |
| Oil phase | |
| Avocado oil | 2.0 |
| Quat. amm. salt | 0.4 |
| Polyoxyethylene 21-stearyl ether | 2.0 |
| Stearyl alcohol | 1.0 |
| Isopropyl palmitate | 1.25 |
| Mineral oil (liquid paraffin) | 4.0 |
| Polypropyleneglycol-lanolin-5-ether | 0.75 |
| Stearic acid | 0.25 |
| Propyl paraben | 0.1 |
| Vitamin E | 0.1 |

"Quat. Amm. Salt" = Quaternary ammonium salt derived from castor oil as described in Example 1.

The oil phase and the aqueous phase were formed separately by mixing the ingredients thereof, both phases were then warmed to 70° C. and the oil phase was added to the aqueous phase with intensive mixing. The resulting emulsion was cooled to 30° C.

Samples of the moisturizing lotion were stored at, respectively, room temperature, 35° C., and 45° C.; all the samples were stable and showed no change in appearance (i.e., there was no phase separation) after two months.

In user tests, it was found that the lotion could be readily rubbed into the skin.

The specific compounds of formula I, and the intermediate, referred to above, can equally and, indeed, more correctly, be named as follows:

Example 1 (i)—title compound
Propane-1,2,3-triyltris [carbonyloxy-(heptadec-8-ene-1,11-diyl)-oxycarbonylchloromethane]

Example 1 (ii)—title compound
Propane-1,2,3-triyltris [carbonyloxy-(heptadec-8-ene-1,11-diyl)-oxycarbonylmethylene-N,N-dimethyl-N-octadecylammonium chloride]

Example 2—title compound
Propane-1,2,3-triyltris [carbonyloxy-(heptadec-8-ene-1,11-diyl)-oxycarbonylmethylene-N,N-dimethyl-N-dodecylammonium chloride]

I claim:

1. Triglyceride quaternary ammonium compounds according to the formula

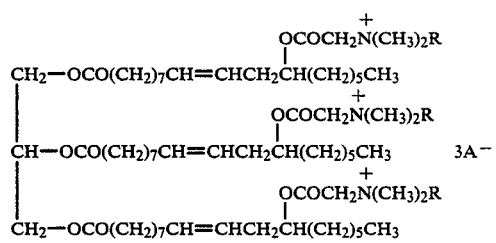

in which R is an alkyl group having 10 to 20 carbon atoms, and $A^-$ is a physiologically acceptable anion.

2. A compound according to claim 1, in which R is n-dodecyl or n-octadecyl.

3. A compound according to claim 1, in which $A^-$ is chloride.

4. A process for the preparation of a compound as defined in claim 1, which comprises reacting triglyceryl ricinoleate with chloroacetyl chloride to esterify the hydroxyl groups of the triglyceride, and reacting the product obtained with an alkyldimethylamine of the formula $N(CH_3)_2R$, where R has the meaning specified in claim 1.

5. A process according to claim 4, further including replacing the chloride anion in the product thereof with another anion $A^-$.

6. A process according to claim 4, in which chloroacetyl chloride is reacted with castor oil as the source of triglyceryl ricinoleate, without separation of the product obtained from the other constituents of the castor oil.

7. A process according to claim 4, in which a stoichiometric excess of chloroacetyl chloride is used.

8. A moisturizing lotion or cream which comprises an effective amount of a compound as defined in claim 1, in which R is an alkyl group having 16 to 20 carbon atoms and a lotion or cream carrier.

9. A hair conditioning composition which comprises an efective amount of a compound as defined in claim 1, in which R is an alkyl group having 16 to 20 carbon atoms and a cosmetic carrier.

10. An anti-microbial composition which comprises an effective amount of a compound as defined in claim 1, in which R is an alkyl group having 10 or 12 carbon atoms and a carrier.

* * * * *